_United States Patent_ [19]

Papaioannou et al.

[11] Patent Number: 5,907,406
[45] Date of Patent: May 25, 1999

[54] DEVICE FOR AND METHOD OF FORMING AN IMAGE OF A TURBID MEDIUM

[75] Inventors: Dimitrios Papaioannou, Athene, Greece; Gert W. 't Hooft, Eindhoven, Netherlands; Martinus B. Van Der Mark, Eindhoven, Netherlands; Sel B. Colak, Eindhoven, Netherlands

[73] Assignee: U.S. Philips Corporation, New York, N.Y.

[21] Appl. No.: 08/909,917

[22] Filed: Aug. 12, 1997

[30] Foreign Application Priority Data

Aug. 14, 1996 [EP] European Pat. Off. .............. 96202284

[51] Int. Cl.$^6$ .................................................. G01B 21/00
[52] U.S. Cl. ........................... 356/432; 356/445; 600/476
[58] Field of Search .................................... 600/476–478; 382/128, 131; 5/601, 607, 610; 356/432–435, 244, 246, 445–446; 378/18

[56] References Cited

U.S. PATENT DOCUMENTS

| | | | |
|---|---|---|---|
| 3,963,933 | 6/1976 | Henkes, Jr. ................................ | 378/18 |
| 3,973,126 | 8/1976 | Redington et al. .......................... | 5/601 |
| 4,015,836 | 4/1977 | Redington et al. .......................... | 5/601 |
| 5,441,054 | 8/1995 | Tsuchiya .................................. | 356/39 |
| 5,477,051 | 12/1995 | Tsuchiya .................................. | 356/432 |
| 5,526,118 | 6/1996 | Miyagawa et al. ...................... | 356/349 |
| 5,596,987 | 1/1997 | Chance .................................... | 600/476 |

FOREIGN PATENT DOCUMENTS

WO9523961 8/1995 WIPO .

OTHER PUBLICATIONS

"Fundamentals of Image Processing" A.K. Jain, Prentice Hall, 1989, pp. 439–441.
"Monte Carlo Simulations of Photon Migration Path Distributions in Multiple Scattering Media" by Shechao Feng and Fanan Zeng, Spie vol. 1888, pp. 78–89 in Progress in Biomedical Optics, Proceedings of Photon Migration and Imaging in Random Media and Tissues Jan. 1993, Los Angeles, CA.

_Primary Examiner_—Robert Kim
_Attorney, Agent, or Firm_—Dwight H. Renfrew, Jr.

[57] ABSTRACT

A device for imaging a turbid medium, for example a breast of a female, includes a holder for receiving the turbid medium, a light source, a photodetector and a processing unit for deriving the image from the intensities measured. The holder is adapted to receive besides the turbid medium also an adaptation medium having substantial identical optical parameters as the optical parameters of the turbid medium. In this way artefacts in the reconstructed image due to the boundary effect between the turbid medium and the holder can be reduced. When a liquid is used as the adaptation medium a perfect match between the holder and the shape of the turbid medium can be obtained. Further, also intensity differences in the image due to different path lengths between light source and photodetector can be equalized.

20 Claims, 4 Drawing Sheets

DEVICE FOR AND METHOD OF FORMING AN IMAGE OF A TURBID MEDIUM

RELATED APPLICATION

This application is related in subject matter to commonly owned application Ser. No. 09/909,915 naming Sel B. Colak as inventor which is filed simultaneously with and has the same title as this application, and which application is incorporated herein by reference in its entirety.

BACKGROUND OF THE INVENTION

1. Field of the Invention

The invention relates to a device for imaging a turbid medium, the device including a holder for receiving the turbid medium, a light source for irradiating the turbid medium, a photodetector for measuring the intensity of the light emanating from the turbid medium, and a processing unit for deriving an image of the turbid medium from the intensities measured.

The invention also relates to a method of forming an image of a turbid medium, which method includes: irradiating the turbid medium by means of light at a plurality of positions, measuring the intensity of the light emanating from the turbid medium at a plurality of positions, and deriving an image of the turbid medium from the intensities measured.

2. Description of Related Art

For the purposes of this patent application with a light source is intended a source of electromagnetic radiation with a wavelength in the visible or infra-red range between approximately 500 and 1000 nm. A device and method of this kind are known from WO 95/23961. The known device is used for imaging an internal structure of biological tissue. In medical diagnostics the known device could be used for imaging the internal structure of breast tissue of a human female. For example, a growth of a tumor can be localized in such an image. A disadvantage of the known device is that the image of the internal structure of the turbid medium contains artefacts along the outer surface of the turbid medium.

SUMMARY OF THE INVENTION

It is an object of the invention to reduce the artefacts along the outer surface of the turbid medium by reducing the boundary effects on the image. To this end, the device in accordance with the invention is characterized in that the holder is also arranged to comprise an adaptation medium having optical properties by which boundary effects between the turbid medium and its surroundings are significantly reduced. As a result contours of equal density of a photon path distribution between the light source and the photodetector corresponds to an ellipsoid-shape because of substantial absence of boundary effects between the adaptation medium and the turbid medium. The photon path distribution represents the influence of a small absorbing object on the measured light when the absorbing object is placed at a position between the source and the photodetector of a particular source detector combination.

A further advantage consists in that excessive intensity differences in various measurement geometries, for example, a parallel plate geometry or a fan beam geometry are counteracted. Without an adaptation medium, measurements with a parallel plate geometry or fan beam geometry give rise to differences between intensities measured in positions in which the turbid medium is well enclosed within the holder, so that virtually no light is lost at the surface, and intensities measured in positions near the outer surface of the turbid medium where a non-negligible fraction of the light traverses the outer surface and is lost. As a result of the use of an adaptation medium having substantially identical optical parameters as the turbid medium, the light paths between the light source and photodetector are similar in all positions, so that said intensity differences are reduced. Further, relevant optical parameters that could be adapted are e.g. the absorption parameter $\mu_a$ and the transport or reduced scattering parameter $\mu_s'$ of the adaptation medium. A description of the absorption parameter $\mu_a$ and the transport or reduced scattering parameter $\mu_s'$ can be found in, inter alia, Monte Carlo Simulations of Photon Migration Path distributions in Multiple Scattering Media, by S. Feng et al, SPIE, vol 1888, 1993, page 78–89.

A special embodiment of the device in accordance with the invention is characterized in that the holder is arranged to comprise a liquid as the adaption medium. As a result, the shape of the adaptation medium can be matched perfectly with the turbid medium and the optical parameters of the adaptation medium could be adapted by a choice of the optical parameters of the liquid.

A further embodiment of the device in accordance with the invention is characterized in that an absorption characteristic of the liquid comprises a slope in a range around a centre wavelength, the range comprising a wavelength of light to be generated by the light source. For a liquid with that absorption characteristic the attenuation coefficient of the liquid can be matched to a range of different attenuation coefficients of the turbid medium by altering the wavelength of the light generated.

A further embodiment of the device in accordance with the invention is characterized in that for said slope a ratio of about 3.5 exists between an absorption for a first wavelength at the beginning of the range and an absorption for a second wavelength at the end of the range. Absorption characteristic of the liquid comprising such slopes can be obtained by addition of dyes, such as Patent Blue V (E131) or Indigo Carmine (E132). Both dyes possess both an absorbance characteristic comprising a slope in a range of 10 nm around a centre wavelength of about 660 nm.

A further embodiment of the device in accordance with the invention is characterized in that the light source comprises a laser. By application of a laser the wavelength of the light to be generated can be adjusted in a small range around the centre wavelength of, for example, about 10 nm by for example, control of the operating temperature of the laser.

A further embodiment of the device in accordance with the invention is characterized in that the light source is adapted to generate light having a substantially constant intensity. This has the effect that simple photodetectors and low frequency electronic circuits can be used in the device. In several known devices for imaging of turbid media a modulated light source is employed and therefore expensive photo-multiplier tubes and high frequency electronics circuits are necessary for the detection of light emanating from the turbid medium.

The invention also relates to a method of forming an image of a turbid medium, characterized in that during measuring the intensities an adaptation medium is placed in contact with the turbid medium, the adaption medium having optical properties such that boundary effects between the turbid medium and its surroundings are significantly reduced.

A special embodiments of a method according to the invention is characterized in that a liquid is used as an adaption medium.

The further embodiment of a method according to the invention is characterized in that for matching the optical properties of the adaption medium to the optical properties of the turbid medium a dye is added to the liquid.

As a result, the optical properties of the adaptation medium could be easily adjusted to the optical properties of the turbid medium.

A further embodiment of a method according the invention is characterized in that the method comprises a further step in which a wavelength of the light to be generated is adjusted such that for the adjusted wavelength an attenuation coefficient of the liquid substantially equals that of the turbid medium. By adjusting the wavelength of the light to be generated within a small range of about 10 nm an absorption of the liquid can be varied by, for example, a ratio of 3.5. That ratio is sufficient to cover a wide range in attenuation coefficients of breast tissue of different women.

A further embodiment of a method according to the invention is characterized in that a commercially available suspension for cosmetic purposes is used. An advantage of the use of a commercially available suspension for cosmetic use, e.g. a body milk, as an adaptation medium is that the body milk is thoroughly tested on the absence of harmful effects on the human body and likely to be readily accepted by any person to be investigated.

These and other aspects of the invention will be apparent from and elucidated with reference to the embodiments described hereinafter.

DETAILED DESCRIPTION OF THE PREFERRED EMBODIMENTS

Figure 1:
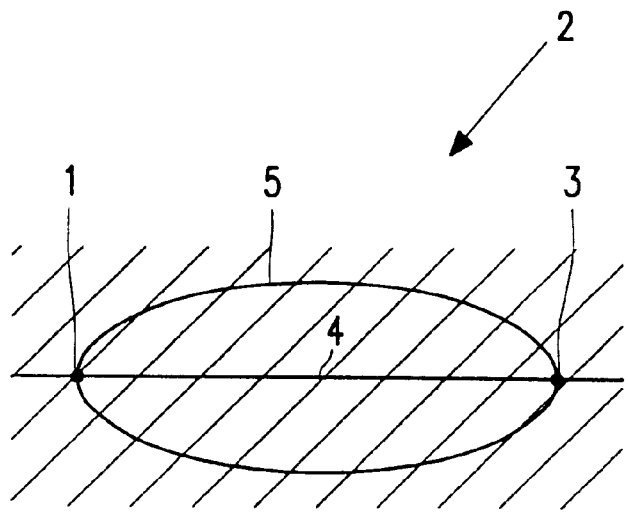
FIG. 1 shows a photon path distribution in a homogeneous turbid medium.

FIG. 1 shows by way of example the photon path distribution between a light source 1 and a photodetector 3 in an infinite homogeneous turbid medium 2. The photon path distribution is used to describe the transport of light in a turbid medium. This description is known from, inter alia, Monte Carlo Simulations of Photon Migration Path distributions in Multiple Scattering Media, by S. Feng et al, SPIE, vol 1888, 1993, page 78–89. The contours of equal density of the photon path distribution in the infinite homogeneous turbid medium 2 correspond to ellipsoid-like shapes, like the indication by 5 in FIG. 1, a major axis 4 of which coincides to the heart line of the photon path distribution. The photon path density function peaks along this line between the light source and the photodetector. Curved lines further outward correspond to lower photon path densities.

Figure 2:
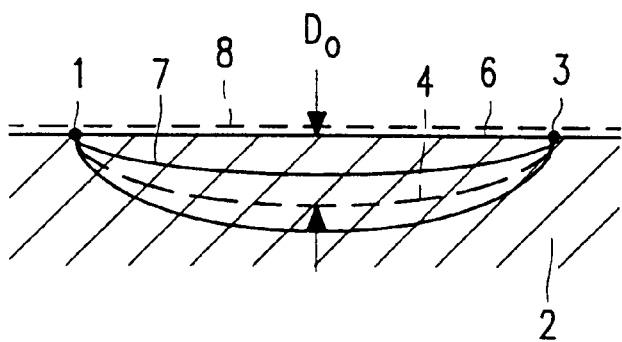
FIG. 2 shows a photon path distribution in a semi-infinite turbid medium.
Figure 3:
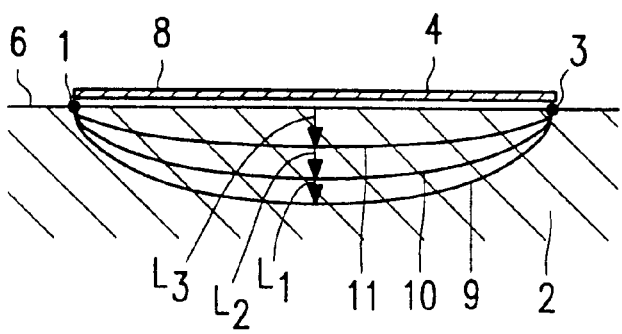
FIG. 3 shows various heart lines between light source and photodetector in a turbid medium for different properties of the adaptation medium.

However, if a semi-infinite medium is used and the light source 1 and the photodetector 3 are situated at some distance from one another on the boundary surface 6, the shape of the photon path distribution will be distorted by photons leaving the turbid medium. FIG. 2 shows a distorted photon path distribution 7 in a semi-infinite turbid medium 2. As is shown in FIG. 2, the heart line 4 of the distorted photon path distribution has been deflected with respect to the connecting line between the light source 1 and the photodetector 3, i.e. towards the interior of the turbid medium 2. The reference $D_o$ in FIG. 2 denotes the distance between the deflection of the heart line of the photon path distribution and the connecting line between the light source 1 and the photodetector 3. The invention relates to the arrangement of an adaptation medium 8 along the boundary surface 6 of the turbid medium 2 in order to influence the heart line 4. An optical parameter, for example, the reflection coefficient of the adaptation medium 8, or a combination of absorption and scattering parameters influences the quantity of photons leaving the turbid medium 2 via the boundary surface 6. The shape of the photon path distribution 5 between the light source 1 and the photodetector 3 in the turbid medium 2 thus changes. FIG. 3 illustrates the change of the position of the heart line for different values $R_i$ of the reflection coefficient on the boundary surface 6. As is shown in FIG. 3, the heart line of the photon path distribution is deflected away from the boundary surface for a decreasing reflection coefficient. In FIG. 3 the distance between the connecting line and the heart line is denoted with L. If the reflection coefficient of the adaptation medium 8 has approximately the value zero, said distance L has the value $L_1$. If the reflection coefficient has a fixed value $R_1$ in the range between 0 and 1, said distance L has the value $L_2$ with $L_2<L_1$. If the reflection coefficient has a second fixed value $R_2$ in the range between $R_1$ and 1, said distance L has the value $L_3$ with $L_3<L_2$. If the reflection coefficient has a value of approximately 1, said distance L becomes approximately 0.

Figure 4:
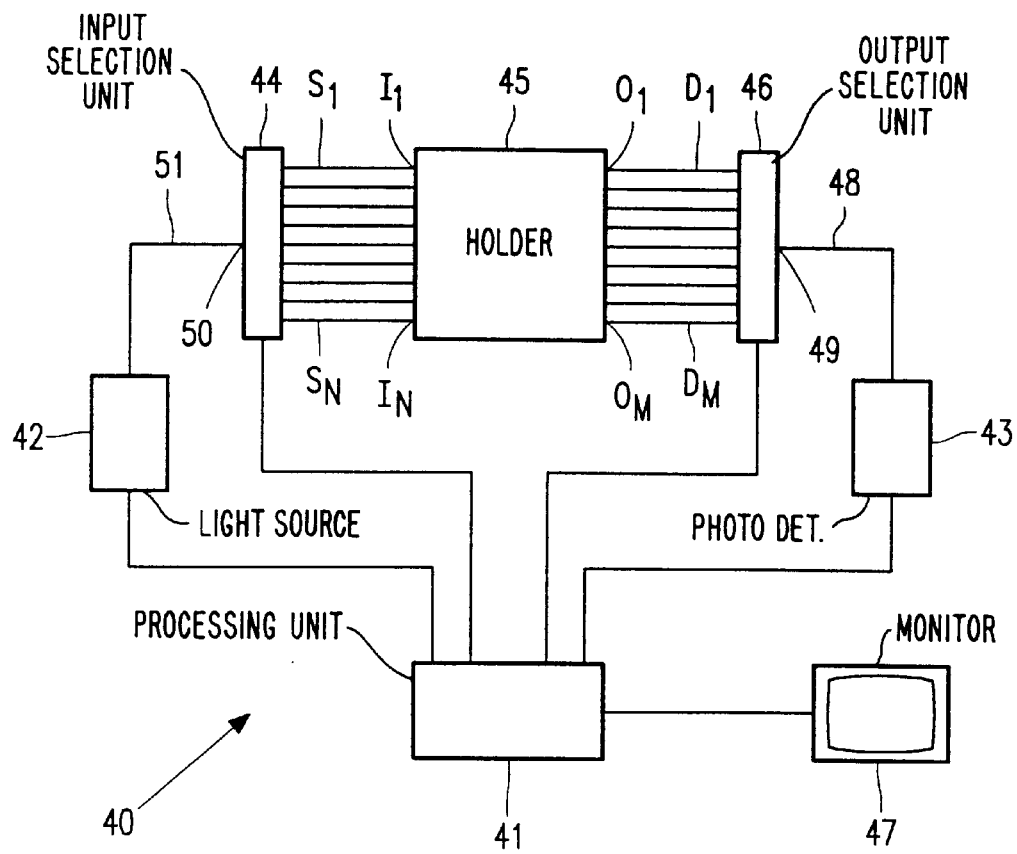
FIG. 4 shows a mammography device for forming an image of an internal structure of the turbid medium.

The invention will be described with reference to the FIG. 4 in which, by way of example, a mammography device 40 is shown. The device in accordance with the invention has been described for a mammography system, but it can likely be used also for examination of other parts of a human or animal body or for testing other highly scattering materials. The device is intended to detect inhomogeneities in the tissue of a female breast. Examples of such inhomogeneities are increased microvascularizations or a high concentration of small blood vessels around a malignant tumor. The device in accordance with the invention is arranged to image and detect such anomalies when they are still very small, so that a carcinoma can be discovered at an early stage, however, without subjecting the patient to the risks of examination by means of ionizing radiation, for example X-rays.

The mammography device in accordance with the invention is provided with a holder 45 which is arranged to receive a part of a turbid medium, and also an adaptation medium. The mammography device 40 also comprises a light source 42 for generating light, a photodetector 43 for detecting light emanating from the turbid medium, a processing unit 41 for deriving an image from the measured intensities, and monitor 47 for the display of images. The generated light may have either a substantially constant intensity or an amplitude-modulated intensity and a wavelength being in the range between, for example 500 and 1000 nm. The light source may comprise, for example a semi-conductor laser or light emitting diode. Another possibility is that the light source comprises of several semi-conductor lasers, each semi-conductor laser having a different wavelength in the interval between 500 and 1000 nm, and a selection switch to select one of the semi-conductor lasers. This arrangement allows to obtain optimal contrast of a reconstructed image for different optical characteristics of the turbid medium. The photodetector 43 is arranged for detecting the light which may be coupled with the turbid medium tissue via the output ports $O_1 \ldots O_M$ and an optical conductor 48. The photodetector 43 may comprise, for example a photomultiplier tube or a PIN photodiode via optical ports $O_1 \ldots O_N$. Other configurations with relation to the photodetectors are also possible. For example, a configuration, in which each of the output ports $O_1 \ldots O_M$ is coupled to a separate photodetector and the outputs of the photodetectors are measured in parallel. Especially when the generated light has a substantial constant amplitude the use of photodiodes in combination with low frequency electronic circuits provides an economic solution when multiple photodiodes are employed.

In order to carry out intensity measurements of the turbid medium the holder 45 comprises a first number of N input ports $I_1 \ldots I_N$ and a second number of M output ports $O_1 \ldots O_M$ whose positions relative to one another on the holder 45 are known. The input ports $I_1 \ldots I_N$ are coupled, via optical conductors $S_1 \ldots S_N$, to the outputs of an input selection unit 44 whose input 50 is coupled to the light source 42 via an optical conductor 51. The output ports $O_1 \ldots O_M$ are coupled, via optical conductors $D_1 \ldots D_M$, to the inputs of an output selection unit 46 whose output 49 is coupled to a photodetector 43 via an optical conductor 48. In practice, 256 input ports and 256 output ports can be used. Also other numbers are possible, for example 128 input ports and 128 output ports. It is remarked that the number of output ports M need not necessarily be equal to the number of input ports N. During measurement the input ports $I_1 \ldots I_N$ are coupled to the light source 42 and the output ports $O_1 \ldots O_M$ are coupled to the photodetector 43. Coupling taking place in a specific order and the light being radiated into the turbid medium, via the input ports. A part of the light emanating from the turbid medium is conducted to the photodetector 43 via the output ports $O_1 \ldots O_M$ and the optical conductors $D_1 \ldots D_M$, the measured intensities being stored by the processing unit 41.

Per measurement an intensity of the light originating from the selected input port $I_i$ is measured on a selected output port $O_j$ so as to be stored in the processing unit 41. Subsequently, the measurements are executed, all combinations of light sources and photodetectors then being measured with a first value $R_1$ of the effective reflection of the adaptation medium with respect to the turbid medium tissue. After the execution of the measurements, an array of intensity values are then available for the reconstruction of an image. Subsequently, the processing unit 41 can derive an image of the internal structure of the beast tissue from the measured intensities. The image can subsequently be displayed on a monitor 47. The image is derived from the measured intensities using projection reconstruction. Projection reconstruction is known inter alia from X-ray computed tomography and from "Fundamentals of Image Processing" by A. K. Jain, Prentice Hall, 1989, pp. 439–441.

To reduce the artefacts near the outer surface of the image of the internal structure of the turbid medium formed by the mammography device in accordance with the invention consists in using a liquid adaptation medium besides the turbid medium in the holder, which liquid adaptation medium has optical parameters $\mu_a$ and $\mu_s'$ which reasonably match the mean optical parameters of the turbid medium. An indication that the optical parameters of the adaption medium have matching optical parameters could be found in that in the reconstructed image the intensity of the turbid medium is approximately equal to the intensity of the adaptation medium in the reconstructed image.

Figure 5:
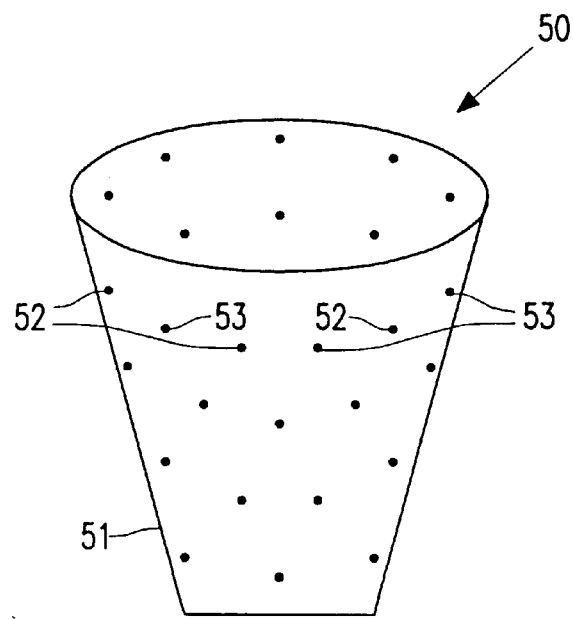
FIG. 5 shows a first type of holder of the mammography device for carrying out measurements by means of a fan beam geometry.

The device according to the invention can be provided with different types of holders for measurements with various geometries. The holders are described in relation to FIG. 5 and FIG. 6. FIG. 5 shows an example of a holder of the mammography device 40 which is intended to receive a liquid adaptation medium. The holder 50 is intended to carry out a measurement with a fan-shaped beam geometry in the mammography device 40. The holder 50 comprises a bowl-shaped or conical part 51 for receiving a liquid adaptation medium and a part of the breast of a female. In the wall of the bowl-shaped part there are provided N input ports and M output ports, said ports being arranged in circles. This is illustrated in FIG. 5, showing three input ports 52 and three output ports 53 arranged on a circle. In practice a holder of the first type may comprise 128 or 256 input ports and output ports. The spacing of the input ports and the output ports must be known for the reconstruction of an image and preferably remains constant during the execution of the measurements. The holder 50 can be coupled to the mammography device 40 by means of optical conductors. The input ports $I_i \ldots I_N$ can then be coupled to the light source 42 via optical conductors $S_1$ to $S_N$ and the input selection unit 44. The output ports $O_1 \ldots O_M$ can be coupled to the photodetector 43 via the optical conductors $D_1$ to $D_N$, the output selection unit 46 and the optical conductor 48. For the execution of the measurements the input ports and output ports can be chosen so that a two-dimensional or three-dimensional image of the internal structure can be derived from the measured intensities. For the liquid adaptation medium use can be made of, for example a intralipid solution or a cosmetic liquid, a so-called body milk. The optical parameters $\mu_a$ and $\mu_s'$ of those liquids can be adapted to the mean values $\mu_a$ and $\mu_s'$ of the turbid medium in order to obtain images with reduced boundary effects. The mean optical parameters $\mu_a$ and $\mu_s'$ of the breest tissue could be determined in a separated step. The optical parameters $\mu_a$ and $\mu_s'$ of the body milk can be adapted by dilution or by addition of dyes.

In order to match an attenuation coefficient of the liquid with an attenuation coefficient of the breast tissue a concentration of dyes or scatterers in the liquid can be adapted. As a result both the scattering coefficient $\mu_s'$ as well as the absorbing coefficient $\mu_a$ can be influenced and the attenuation coefficient $\kappa=\sqrt{3\mu_s'\mu_a}$ can be adjusted. Furthermore, it is assumed for the determination of a concentration of the dye in the liquid that an index of refraction of the liquid comprising an aqueous solution as, for example, Intralipid or a solution of $TiO_2$ water, is substantially equal to an index of refraction of the breast tissue. Under practical conditions it appears that a concentration of scatterers that yield a scattering coefficient $\mu_s' \cong 1.3$ mm$^{-1}$ a wavelength $\lambda=660$ nm, is sufficient to cover most of the experiments.

Figure 8:
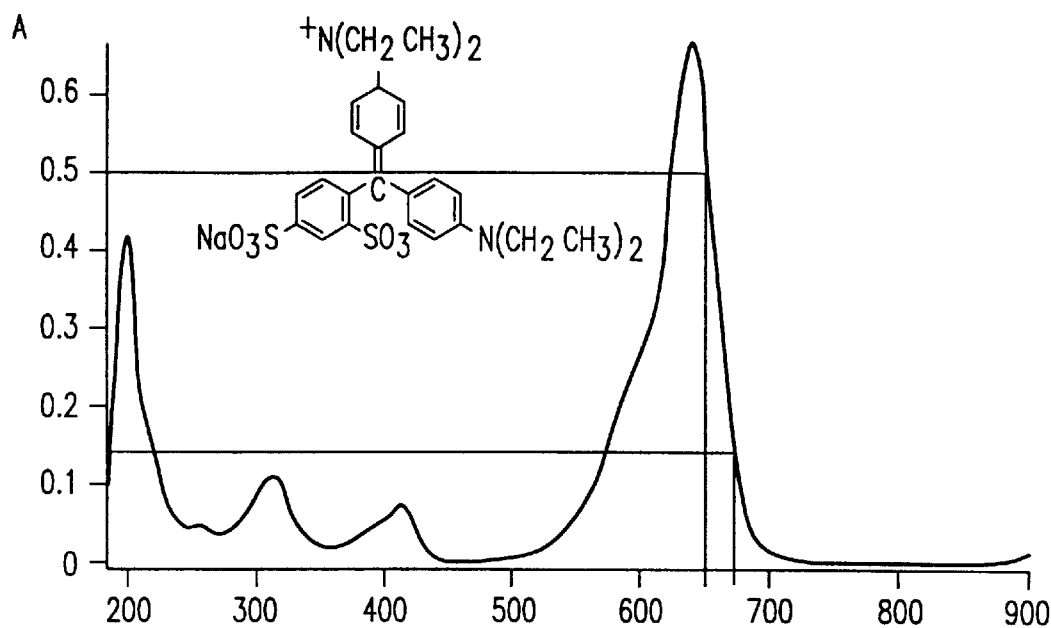
Figure 9:
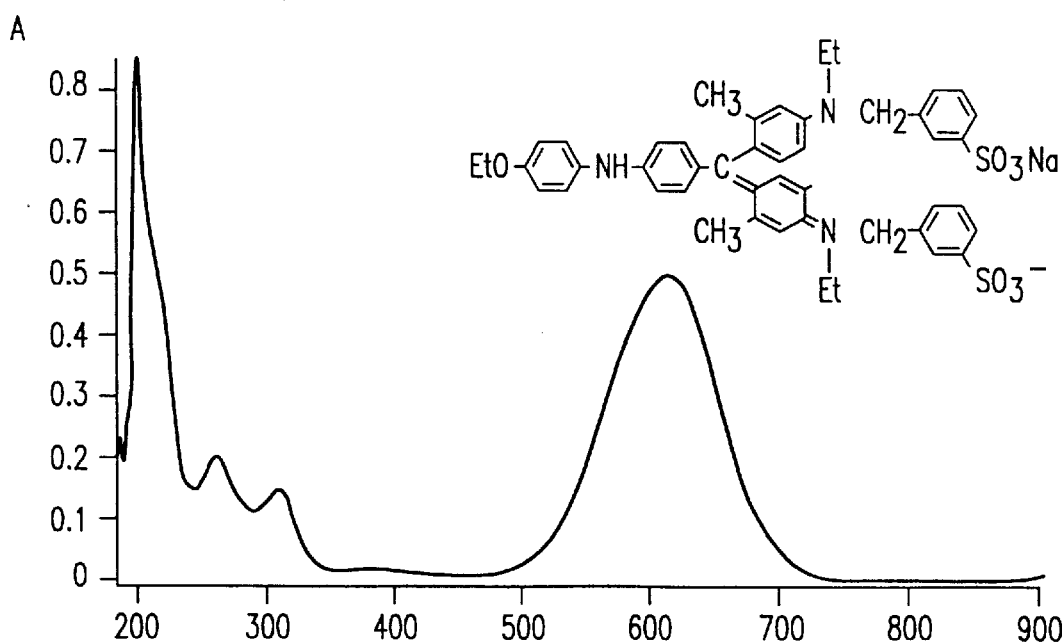

In order to match the attenuation coefficient of the liquid to the attenuation coefficient of the breast tissue the method according to the invention comprises addition to the liquid of a dye possessing an absorption characteristic comprising a slope in a range of 10 nm around a centre wavelength of 660 nm and adaptation of the wavelength of the light source such that the attenuation coefficient of the dye at the adapted wavelength is substantially equal the attenuation coefficient of the breast tissue. The adaptation of the wavelength of the light to be generated can be performed by controlling the operating temperature of the laser 42. Dyes that can be added to the liquid comprises, for example, Patent Blue V (E 131) or Indigo Carmine (E 132). FIG. 8 and FIG. 9 shows examples of absorption characteristics of Patent Blue and Indigo Carmine respectively. These dyes possess absorption characteristics comprising slopes in a range between a first wavelength and a second wavelength of 650 and 700 nm and 620 and 720 nm respectively for which slopes a ratio of about 3.5 exists between an absorption for the first wavelength at the beginning of the range and an absorption for the second wavelength at the end of the range.

In order to determine a concentration of a dye in the liquid reference is made to FIG. 8. From FIG. 8 it is derived that an absorption coefficient for a liquid comprising a fixed concentration of Patent Blue can be varied by a factor 3.6 for a variation a wavelength of + or −10 nm with respect to a centre wavelength of 660 nm. As a result a rate of change of an attenuation coefficient of the liquid can be as much as $\sqrt{3.6}=1.9$. That range of the variation of the attenuation coefficient of the liquid is sufficient to cover the range in variation of the attenuation coefficient of breast tissue of different women. Examples of attenuation coefficients of breast tissue of different women are listed in Table 1.

Table 1 lists the attenuation coefficients for three different wavelengths for several woman of age between 40 and 58 with different breast sizes. According to the invention a concentration of a dye in a liquid can be determined by application of FIG. 8. For a given concentration, for example, c=4.8 mg/L the absorption A can be derived from FIG. 8 and is found to be equal to A=α d for a fixed wavelength and for a thickness d=10 mm of a sample. For a wavelength of 650, 660 and 670 nm the absorption A is found to be 0.5, 0.32, 0.14 respectively. The absorbing coefficient $\mu_a$ of the dye can then be determined for the given concentration c as $\mu_a^{dye}$=A log(10)/d=0.23026A. From table 1 an average attenuation coefficient of breast tissue for a wavelength of 660 nm is determined, for example, a value of $\kappa=120$ m$^{-1}$=0.120 mm$^{-1}$. For $\mu_s'$ is 1.3 mm$^{-1}$ and $\kappa=\sqrt{3\mu_{s'}\mu_a}$ the absorption is found to be $\mu_a=\mu_a^{H_2O}+\mu_a^{dye}$=3.7× 10$^{-3}$ mm$^{-1}$. At a wavelength of 660 nm the absorbing coefficient of H$_2$O $\mu_a^{H_2O}$ has the value 6.1×10$^{-4}$ mm$^{-1}$. Hence the absorption coefficient of the dye $\mu_a^{dye}$ has the value of 3.1×10$^{-3}$ mm$^{-1}$. The concentration of the dye is then calculated by $$c = 4.8 \frac{\mu_a^{dye}}{0.23026A} = 0.20 \,\mathrm{mg}/l,$$

wherein A represents the absorption of the dye, which can be found from FIG. 8. At a wavelength of 660 nm the absorption of the dye equals 0.32.

An advantage of the method according to the invention is that a stock of a single liquid with a fixed concentration can be employed for experiments with different women instead of a stock with several liquids of different concentrations. A further advantage is that a matching process can be performed automatically by the processing unit for each experiment.

Figure 6:
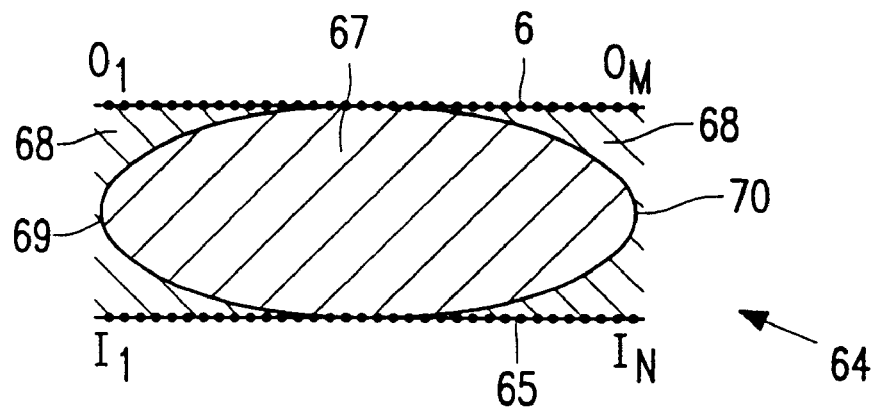
FIG. 6 shows a second type of holder of the mammography device for carrying out measurements with a parallel plate geometry.

A further holder suitable for use in the mammography device 40 is, for example a holder for performing measurements with a parallel plate geometry on a turbid medium. FIG. 6 is a plan view of such a holder 64. The holder comprises two substantially parallel transparent plates 65, 66 which are arranged around the breast 67 of a female. This results in an image of a parallel plate geometry with a slab thickness of approximately 6 cm. The breast can be compressed, for example in a mediolaterial or a craniocaudal direction by the plates 65, 66. A first plate 65 of the holder 64 comprises a number of N input ports I$_1$ to I$_N$ for the coupling of optical conductors S$_1$ to S$_N$ and the other transparent plate 66 comprises a second number of M output ports for the coupling of the optical conductors D$_1$ ... D$_M$. The optical conductors S$_1$ ... S$_N$, D$_1$ ... D$_M$ can be coupled to the input selection unit 44 and the output selection unit 46, respectively. The space between the plates and besides the breast is filled with the liquid adaptation medium 68. A substantially perfect optical fit is obtained by using a liquid adaptation medium 68 whose optical parameters $\mu_a$ and $\mu_s'$ correspond to the mean optical parameters $\mu_a$ and $\mu_s'$ of the breast tissue.

Figure 7:
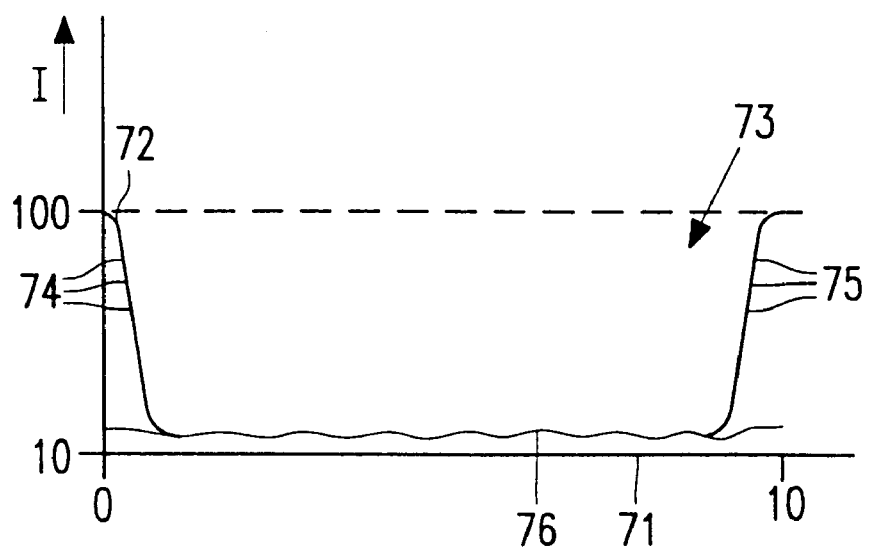
FIG. 7 shows a light intensity distribution of a measurement by means of a parallel plate geometry and FIG. 8 shows an absorption characteristic of Patent Blue (E131) and FIG. 9 shows an absorption characteristic of Indigo Carmine (E132).

A further advantage of the use of a liquid adaptation medium in accordance with the invention consists in that the effects exerted on the light intensity distribution by the interface between the breast and the adaptation medium can be substantially corrected in measurements by means of parallel plate geometry or fan beam geometry; moreover, it is also possible to compensate for an increased intensity due to a shorter light path in the breast between the light source and the photodetector as imposed by the shape of the breast. This will be illustrated in a measurement by means of a parallel plate geometry with reference to FIG. 7. FIG. 7 shows an intensity curve 71 of a measurement with a parallel plate geometry as performed on breast without using an adaptation medium. Near the ends 72, 73 the intensity curve 71 exhibits deviations with respect to positions situated approximately halfway the intensity curve. The ends 72, 73 correspond approximately to the positions 69, 70 where the boundary of the breast 67 in the holder 44 does not adjoin the glass plates 65, 66. The intensity increase is due to the fact that near said points 69, 70 in the breast the light path between light source and photodetector is shorter than a light path between light source and photodetector in the regions in which the breast adjoins the glass plates 65, 66. Because of the intensity differences it will be difficult to detect the disturbances 74, 75 of the intensity near the ends 72, 73 of the curve after reconstruction of the image. The use of the adaptation medium equalizes also the intensity distribution so that the absolute changes can be detected better. The result of the equalization by means of the adaptation medium is represented by the equalized curve 76. The use of a liquid adaptation medium also offers the advantage of a mechanical match between the breast and the holder and as a result of this matching differences in respect of breast size and breast shape can be simply compensated for.

Another possibility is the use of a bag of synthetic material which comprises the liquid adaption medium. This bag can be placed between the holder and the breast and has the advantage that it avoids the loss of any liquid and it could be more comfortable for the woman, which is examined.

Another possibility is the use of a thin sheet of synthetic material placed between the liquid and the breast to avoid a direct contact between skin of the breast and the liquid. In this way the liquid can be used many times.

TABLE I

Optical attenuation coefficient κ for breasts at three wavelengths for volunteers of age between 40 and 58 with differing breast size.

| κ $(m)^{-1}$ | | | $\lambda = 660$ nm | | $\lambda = 780$ nm | | $\lambda = 920$ nm | |
|---|---|---|---|---|---|---|---|---|
| # | age | cup | L | R | L | R | L | R |
| 1 | 54 | B80 | 105 | 111 | 91 | 96 | 168 | 157 |
| 7 | 48 | A75 | 125 | 121 | 117 | 112 | 180 | 182 |
| 9 | 50 | C80 | 101 | 100 | 88 | 88 | 156 | 149 |
| 10 | 57 | B80 | 111 | 104 | 94 | 88 | 152 | 147 |
| 11 | 55 | B80 | 96 | 92 | 81 | 79 | 146 | 142 |
| 12 | 58 | B80 | 108 | 99 | 91 | 88 | 156 | 149 |
| 14 | 52 | D80 | 124 | 115 | 103 | 94 | 151 | 146 |
| 15 | 50 | B75 | 120 | 123 | 99 | 100 | 157 | 155 |
| 17 | 50 | A75 | 120 | 117 | 100 | 101 | 159 | 158 |
| 18 | 54 | B75 | 95 | 91 | 78 | 78 | 152 | 151 |
| 19 | 47 | A70 | 145 | 139 | 130 | 122 | 173 | 168 |
| 20 | 40 | B75 | 163 | 154 | 139 | 138 | 167 | 181 |
| 21 | 45 | B80 | 129 | 129 | 113 | 115 | 161 | 160 |
| 22 | 46 | B85 | 105 | 101 | 97 | 91 | 162 | 154 |
| 28 | 47 | B80 | 99 | 85 | 83 | 82 | 150 | 156 |
| 30 | 53 | B85 | 89 | 84 | 78 | 77 | 152 | 157 |

We claim:

1. A device for forming an image of a turbid medium comprising:
   a holder arranged for receiving both the turbid medium and an adaptation medium, wherein the adaptation medium has one or more wavelength dependent optical properties,
   a light source for irradiating the turbid medium at a selected wavelength such that at the selected wavelength one or more selected optical properties of the adaptation medium are substantially equal to corresponding optical properties of the turbid medium,
   a photodetector for measuring the intensity of the light emanating from the turbid medium, and
   a processing unit for deriving an image of the turbid medium from the measured intensities.

2. The device as claimed in claim 1 wherein the adaptation medium comprises a liquid.

3. A device as claimed in claim 2, characterized in that the light source comprises a laser.

4. The device as claimed in claim 1 wherein the adaptation medium comprises a dye.

5. The device as claimed in claim 4 wherein an absorption characteristic of the adaptation medium comprises a slope in a range around a center wavelength, the range comprising a wavelength of light to be selected from the light source.

6. A device as claimed in claim 5, characterized in that for said slope a ratio of about 3.5 exists between an absorption for a wavelength at the beginning of the range and an absorption for a wavelength at the end of the range.

7. A device as claimed in claim 4, characterized in that the light source comprises a laser.

8. The device as claimed in claim 1 wherein an absorption characteristic of the adaptation medium comprises a slope in a range around a center wavelength, the range comprising a wavelength of light to be selected from the light source.

9. A device as claimed in claim 8, characterized in that for said slope a ratio of about 3.5 exists between an absorption for a wavelength at the beginning of the range and an absorption for a wavelength at the end of the range.

10. A device as claimed in claim 8, characterized in that the light source comprises a laser.

11. A device as claimed in claim 1, characterized in that the light source comprises a laser.

12. The device as claimed in claim 1 wherein the adaptation medium comprises a commercially available suspension for cosmetic purposes.

13. A device as claimed in claim 1, characterized in that the light source is adapted to generate light having a substantially constant intensity.

14. A device as claimed in claim 1, characterized in that the light source comprises a laser.

15. The method as claimed in claim 1 wherein said one or more selected optical properties are an attenuation coefficient.

16. A method of forming an image of a turbid medium comprising:
   arranging along the boundary surface of the turbid medium an adaptation medium with one or more wavelength dependent optical properties,
   selecting a wavelength of light such that at the selected wavelength one or more selected optical properties of the adaptation medium are substantially equal to corresponding optical properties of the turbid medium,
   irradiating the turbid medium by means of light of the selected wavelength at a plurality of positions,
   measuring the intensity of the light emanating from the turbid medium at a plurality of positions, and
   deriving an image of the turbid medium from the measured intensities.

17. The method as claimed in claim 16 wherein the adaptation medium comprises a liquid.

18. The method as claimed in claim 17 wherein the adaptation medium comprises a dye.

19. The method as claimed in claim 17 wherein the adaptation medium comprises a commercially available suspension for cosmetic purposes.

20. The device as claimed in claim 16 wherein said one or more selected optical properties are an attenuation coefficient.

* * * * *